United States Patent [19]

Takei

[11] Patent Number: 5,685,824
[45] Date of Patent: Nov. 11, 1997

[54] PROSTASCOPE WITH A BRIDGE

[75] Inventor: Kazuyuki Takei, Tokyo, Japan

[73] Assignee: Astem Tech Company, Limited, Tokyo, Japan

[21] Appl. No.: 466,658

[22] Filed: Jun. 6, 1995

[30]  Foreign Application Priority Data

Oct. 11, 1994 [JP] Japan .................................. 6-245056

[51] Int. Cl.⁶ .................................................. A61B 1/30
[52] U.S. Cl. ........................ 600/135; 600/105; 600/104; 600/127; 600/129
[58] Field of Search ................................. 600/101, 104, 600/105, 106, 121, 125, 127, 129, 135, 138, 108, 173, 175, 182; 606/16, 18, 10

[56]   References Cited

U.S. PATENT DOCUMENTS

| 3,865,113 | 2/1975 | Sharon et al. | 606/18 |
| 4,608,980 | 9/1986 | Aihara | 606/18 X |
| 4,760,840 | 8/1988 | Fournier, Jr. et al. | 600/101 |

FOREIGN PATENT DOCUMENTS

| 7-136289 | 7/1995 | Japan | 128/4 |
| 2214325 | 8/1989 | United Kingdom | 600/108 |

Primary Examiner—Beverly M. Flanagan
Attorney, Agent, or Firm—Jordan and Hamburg

[57]   ABSTRACT

A prostascope with a bridge includes a guide member which has a guide surface for a laser beam emitting end of a fiber cable at the bottom thereof and which is attached to the tip of the bridge, a reflector which is formed with a slant reflecting surface having a predetermined angle of reflection and which is detachably attached to a mounting portion of the guide member such that the reflector is prevented from rotating relative to the guide member and that a threaded end of the tip of the bride penetrates the reflector, and a cap nut which is removably screwed onto the threaded end of the bridge. The laser beam emitting end of the fiber cable is guided along the guide surface of the guide member and faces the reflecting surface of the reflector, and the tip of a telescope is positioned at a location slightly retracted from the reflection surface of the reflector with the laser beam emitting end of the fiber cable located therebetween so as to visually recognize the entire affected part irradiated with a laser beam emitted from the laser beam emitting end of the fiber cable. This structure allows a surgeon to easily replace the reflector.

16 Claims, 7 Drawing Sheets

PROSTASCOPE WITH A BRIDGE

BACKGROUND OF THE INVENTION

The present invention relates to a prostascope with a bridge which is equipped with a rigid endoscope and which is inserted into the body in a transurethral manner for laser treatments of urinary bladders and urethra, primarily for a prostatectomy to treat the prostatic hypertrophy.

Regarding the related art of this kind, there exists Japanese Patent Application No. 5-286974, filed by the applicant of the present invention, which has already been in practical use. However, operating the prostascope with a bridge according to the aforementioned Japanese Patent Application 5-286974 requires both hands of a surgeon.

Also, the aforementioned Japanese Patent Application uses an operational wire and one end of the operational wire may come off a swing reflecting mirror during treatment, preventing the surgeon from swinging the reflecting mirror. As a result, the surgeon may be forced to cease treatment. In addition, it is quite troublesome to connect one end of the operational wire to the swing reflecting mirror, and the connection is likely to be incomplete.

In the aforementioned prior art, the user is also required to have skill in accurately positioning the laser beam emitting end of a glass fiber cable so that it faces the reflecting mirror at the center thereof. The laser beam emitting end, therefore, will likely be positioned inaccurately.

Since the laser beam emitting end is rather in the free state, it deviates by some chance from the required center position during treatment. Each time it is dislocated, it has to be re-positioned so as to face the reflecting mirror at the center thereof.

Since the surface of the swing reflecting mirror in the aforementioned prior art is flat, it is not easy to finely change the focus of a laser beam. This change also requires advanced skill. The adjustment of the focus of a laser beam has an effect on the surgical accuracy and thus determines surgical quality. Also, there is a problem that some material used in making the swing reflecting mirror is not compatible with some kinds of laser beams.

SUMMARY OF THE INVENTION

Accordingly, an object of the present invention is to overcome the above-mentioned problems of the referenced prior art.

Another object of the present invention is to provide a prostascope with a bridge which allows a used to operate it with one hand.

A further object of the present invention is to provide a prostascope with a bridge which allows a surgeon to easily replace a reflector.

A further object of the present invention is to provide a prostascope with a bridge in which the shape of the reflecting surface of a reflector is changed to change the focus of a laser beam, thereby providing an effective treatment.

Still another object of the present invention is to provide a prostascope with a bridge which allows the material of a reflector to be changed for being compatible with various kinds of laser beams.

A still further object of the present invention is to provide a prostascope with a bridge which allows a user to easily position the laser beam emitting end of a fiber cable so that it faces a reflector at the center thereof.

A still further object of the present invention is to provide a prostascope with a bridge capable of employing an inoperative reflector that does not require frequent replacement.

Other objects of the present invention should be apparent from the specification and drawings, and particularly from the scope of the appended claims.

The aforesaid objectives of the present invention are attained by novel aspects of the present invention described below.

According to the invention, there is provided an improved prostascope with a bridge wherein a fiber cable for transmitting a laser beam and a telescope are respectively inserted from the side and base end of the bridge such that they run along the axis of the bridge, and the bridge is axially inserted from the base end of an outer tube assembly such that the tip of the bridge faces an operational opening which extends along the bottom side of the forward end portion of the outer tube assembly so as to monitor and treat an affected part. The prostascope comprises a guide member which has a guide surface for a laser beam emitting end of the fiber cable at the bottom thereof and which is attached to the tip of the bridge, a reflector which is formed with a slant reflecting surface having a predetermined angle of reflection and which is detachably attached to a mounting portion of the guide member such that the reflector is prevented from rotating relative to the guide member and that a threaded end of the tip of the bride penetrates the reflector, and a cap nut which is removably screwed onto the threaded end of the bridge. The laser beam emitting end of the fiber cable is guided along the guide surface of the guide member and faces the reflecting surface of the reflector, and the tip of the telescope is positioned at a location slightly retracted from the reflection surface of the reflector with the laser beam emitting end of the fiber cable located therebetween so as to visually recognize the entire affected part irradiated with a laser beam emitted from the laser beam emitting end of the fiber cable.

Preferably, one of a plurality of reflectors having different angles of reflection is selectively attached to the guide member.

Preferably, the mounting portion of the guide member is formed by a cylindrical portion which projects from the guide member while forming a step therebetween and which is provided with a pair of pins which radially outwardly extend from the base end of the cylindrical portion.

Preferably, securing grooves are formed in the reflector at opposite sides thereof so that the pins of the mounting portion are fitted thereinto when the reflector is attached to the mounting portion of the guide member.

Preferably, a reflecting groove surface which has an arcuate cross-section having a radius of curvature of about 1.5° is formed in the slant reflecting surface of the reflector.

Preferably, the guide member and the cap nut are made of stainless steel.

Preferably, the reflector is made of a metallic material and is plated with another material so as to reflect a certain kind of laser beams.

Preferably, the reflector is made of brass and plated with gold.

Preferably, an outer tube assembly of a urethrocystoscope for a Kaiba laser beam is used as the outer tube assembly of the prostascope to permit perfusate to flow continuously.

Preferably, the outer tube assembly comprises a cylindrical bridge fixing barrel which is provided with short tubes projected from both sides of the bridge fixing barrel, the tubes being provided with cocks and adapted for effecting communication with the inside of the outer tube in order to lead cleaning liquid, drainage and treating tools thereinto and therefrom, the bridge fixing barrel being fixedly connected to the base end of a urethral tube, and an axially extending operational opening being provided at the bottom side of a warp end portion of the urethral tube.

Preferably, the telescope comprises a connection barrel which is equipped with an eyepiece funnel at the backward end thereof and a light inlet portion at one position on the periphery thereof, the base end of a telescope tube portion being fitted into the forward end of the connection barrel, and the forward end of the connection barrel being detachably fitted into a telescope fixing barrel of the bridge.

Preferably, the outer tube assembly is formed by a tube and a bridge fixing barrel and is adapted to receive therein a mandrel comprising a rod, a closing piece and a plug, and wherein the closing piece is fixed to the forward end of the rod such that the operational opening of the outer tube assembly is closed when the mandrel is inserted into the outer tube assembly, the backward end of the rod is fixed to the plug which has a gripping portion integrally formed therewith, and the plug is fitted into the bridge fixing barrel in a removable manner.

As described above, since an affected part irradiated with a laser beam can be monitored through a fiberscope, operations using the prostascope is free from mistaking a healthy tissue for an affected part, thereby providing excellent safety. Since the prostascope is easy to disassemble and assemble, the cloudy reflector does not require the replacement of the entire prostascope in distinction from conventional laser knives. When the reflector becomes cloudy, the reflector is polished or replaced. Only the reflector, if disabled, is changed, while other members endure a long-term use. Hence, the prostascope with a bridge according to the present invention is very useful and economical.

A fiber cable for a general-purpose laser beam (direct projection type quartz fiber cable) available from the market at low costs can be used with the prostascope of the present invention. A laser beam emitted from the laser beam emitting end of the fiber cable is reflected at the reflector to change an illuminating angle.

By the use of a guide member, the laser beam emitting end of the fiber cable can be easily positioned so as to face the reflector at the center thereof, and can be fixed in place.

A connection with an end of an operational wire is not involved. A surgeon can replace the reflector only by removing a cap nut. Moreover, the surgeon can handle the prostascope of the present invention with one hand during a treatment. This, coupled with a capability of a visual observation of an affected part irradiated with a laser beam, improves the usability of the prostascope to a great extent.

By changing materials of the reflector, the reflector is compatible with various kinds of laser beams. Also, by selecting a reflector having a desired angle of a slant reflecting surface, the focus of a laser beam is changed, and hence the effect of a laser treatment can be modified as desired. Since the reflector has a large heat capacity, it is less likely to be molten by a laser beam. Thus, the prostascope with a bridge according to the present invention is very practical, useful, and effective.

DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DETAILED DESCRIPTION OF THE EXEMPLARY EMBODIMENT

Figure 5A:
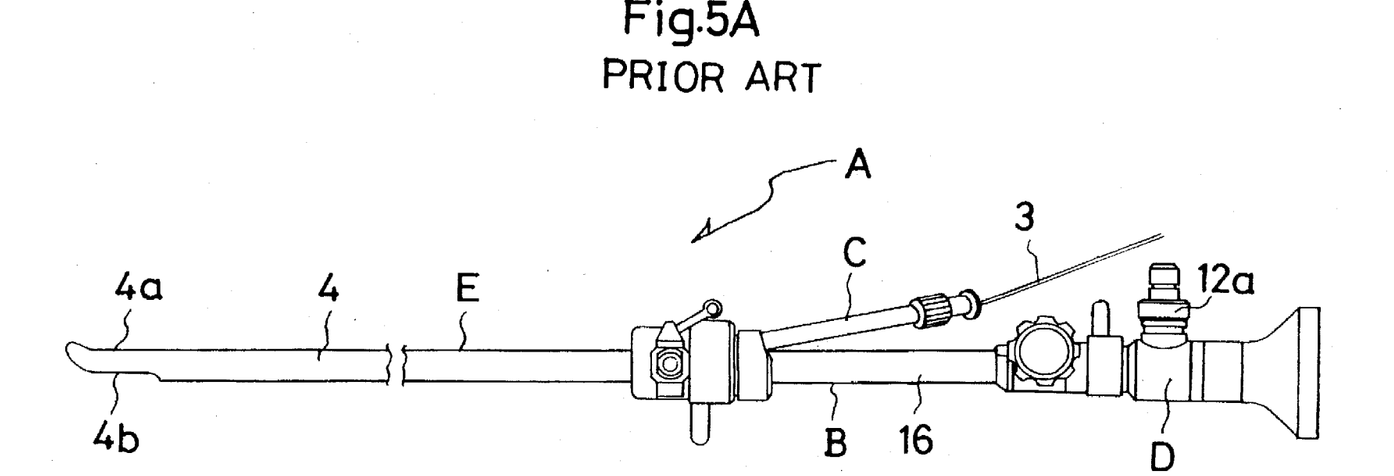
FIG. 5A is a side view of a prostascope with a bridge according to the prior art.
Figure 5B:
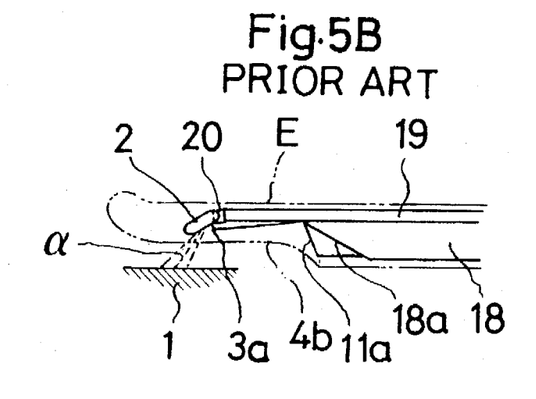
FIG. 5B is an enlarged view of the tip portion of the prostascope according to the prior art in the state where an outer tube assembly is removed.

The prior art of the aforementioned Japanese Patent Application No. 5-286974 will now be described with reference to FIGS. 5A through 9B. In FIGS. 5A and 5B, reference character A denotes a prostascope with a bridge, reference B denotes a bridge, reference character C denotes a glass fiber guide tube for leading into the prostascope a glass fiber cable which transmits a curative laser beam. Reference character D denotes a rod lens telescope inserted into the bridge B, reference character E denotes an outer tube assembly, and reference character F denotes a mandrel.

Figure 6A:
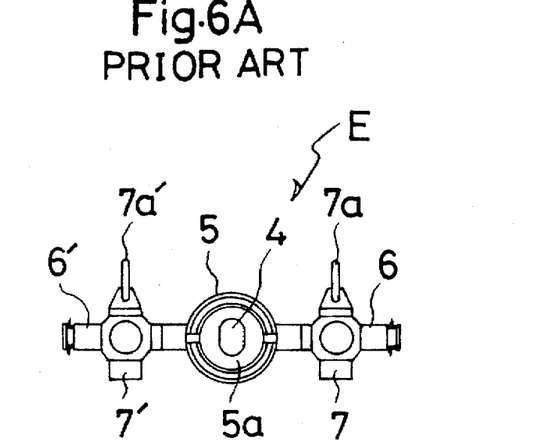
FIG. 6A is an end view of the outer tube assembly according to the prior art.
Figure 6B:
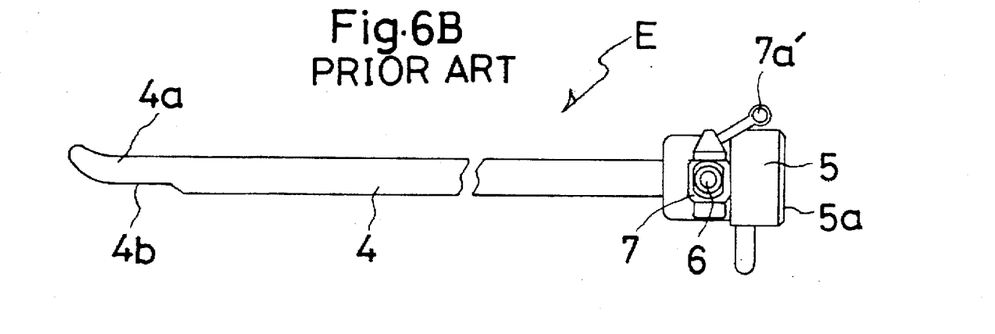
FIG. 6B is a side view of the outer tube assembly according to the prior art with the intermediate portion thereof omitted.
Figure 7:
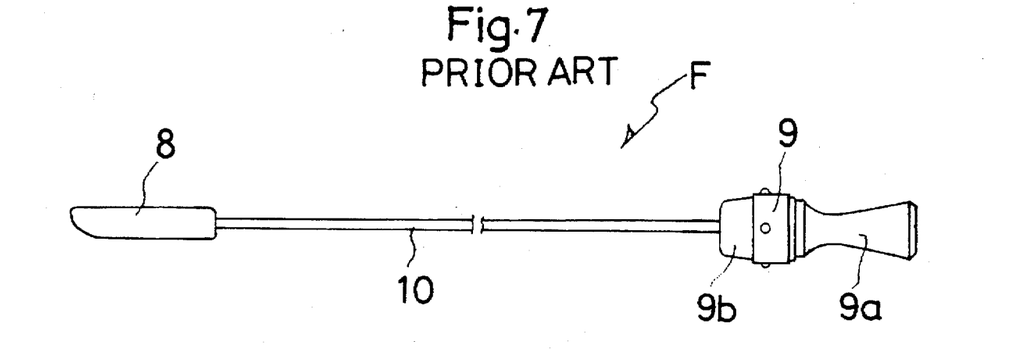
FIG. 7 is a side view of a mandrel according to the prior art in which the mandrel is inserted into the outer tube assembly, when the prostascope is inserted into the human body, in order to block up an opening of the outer tube assembly at the tip thereof, with the intermediate portion thereof omitted.

Numeral 1 denotes an affected part, and numeral 2 denotes a swing reflecting mirror. Numeral 3 denotes a glass fiber cable for leading a curative laser beam to an affected part therethrough, and numeral 3a denotes a laser beam emitting end. As shown in FIGS. 6A and 6B, the outer tube assembly E comprises a urethral tube 4 and a bridge fixing barrel 5. The urethral tube 4 will be inserted into the urethra. Numeral 4a denotes a warp end portion, and numeral 4b denotes an operational opening which extends along the bottom side of the warp end portion 4a. The bridge fixing barrel 5 has a fitting bore 5a into which the bridge B is inserted. Numerals 6 and 6' denote short tubes for introducing a cleaning liquid, drainage and treating tools into or out from the outer tube assembly, numerals 7 and 7' denote cocks to allow/block the passage of supplied/drained perfusate and treating tools, and numerals 7a and 7a' denote cock levers. As shown in FIG. 7, the mandrel F which is inserted into the outer tube assembly 4 is composed of a closing piece 8, a rod 10, and a plug 9. The closing piece 8 is attached to the tip of the rod 10 so as to block up the operational opening 4b of the outer tube assembly E when the mandrel F is inserted in the outer tube assembly E. The plug 9 is attached to the rear end of the rod 10 and has a gripping portion 9a continuously formed with the plug 9 at its rear side, and a forward end portion 9b which is fitted into the fitting bore 5a of the bridge fixing barrel 5 in a removable manner.

Figure 8A:
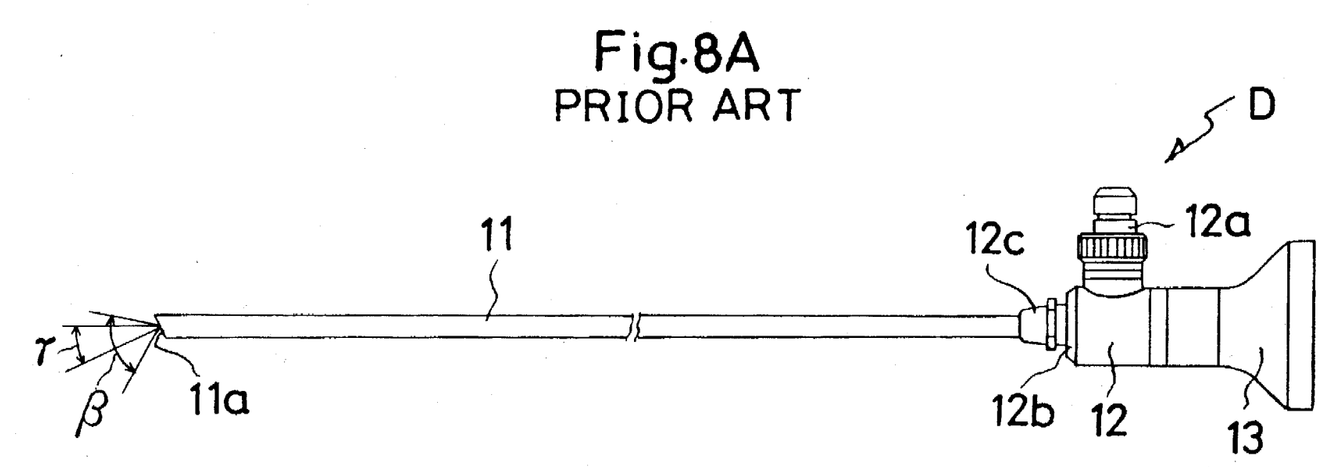
FIG. 8A is a side view of a rod lens telescope according to the prior art with the intermediate portion thereof omitted.
Figure 8B:
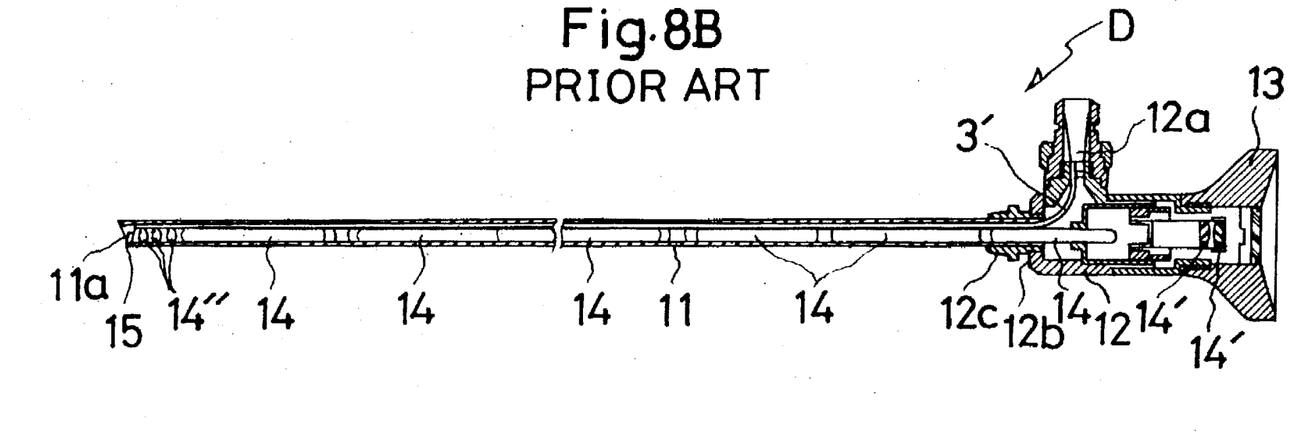
FIG. 8B is a cross-sectional view of the rod lens telescope according to the prior art with the intermediate portion thereof omitted.

As shown in FIGS. 8A and 8B, the rod lens telescope D comprises a telescope tube portion 11 which contains lenses and a glass fiber cable 3' for transmitting a laser beam for diagnosis. Numeral 11a denotes a tip of the tube portion 11 which is diagonally cut. Numeral 12 denotes a connection barrel having a light inlet portion 12a which is connected with the glass fiber cable 3' and which is projected upward from the connection barrel 12. The telescope tube portion 11 is inserted into the forward end 12b of the connection barrel 12 through a mouthpiece 12c.

Numeral 13 denotes an eyepiece funnel, numeral 14 denotes lenses, numeral 14' denotes an eyepiece, numeral 14" denotes an objective lens, and numeral 15 denotes a prism.

Figures 9A, 9B:
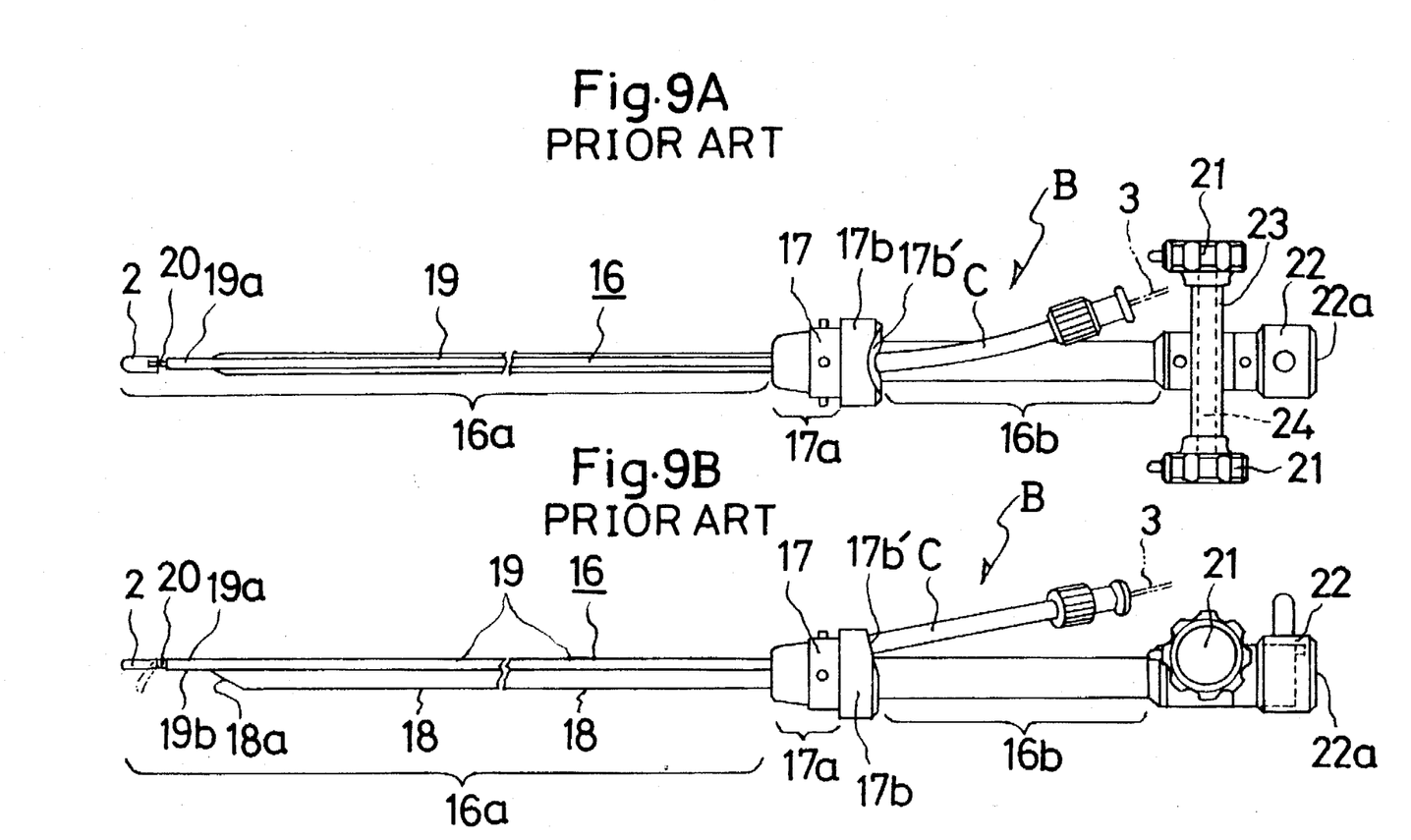
FIG. 9A is a plan view of the bridge according to the prior art with the intermediate portion thereof omitted.
FIG. 9B is a side view of the bridge according to the prior art with the intermediate portion thereof omitted.

As shown in FIGS. 9A and 9B, the bridge B comprises a bridge tube portion 16 and a junction plug 17. The bridge tube portion 16 is composed of an insert portion 16a which is to be inserted into the outer tube assembly E and an external tube portion 16b into which the rod lens telescope D is fitted. The insert portion 16a and the external tube portion 16b are connected through the junction plug 17. The junction plug 17 has a forward portion 17a to be fit into the fitting bore 5a of the bridge fixing barrel 5 in a removable manner, and a flange 17b wherein the glass fiber guide tube C projects from a slant surface 17b' formed at the rear end of the flange 17b.

Numeral 18 denotes a sheath tube into which the telescope tube portion 11 of the rod lens telescope D is inserted and which has a diagonally cut opening 18a at its tip. Numeral 19 denotes an operational tube which extends along the entire length of the sheath tube 18 and has a tip 19a projected from the tip of the sheath tube 18 and through which a glass fiber cable 3 and an operational wire (not shown) for a swing reflecting mirror 2 are passed. Numeral 20 denotes a mounting piece fitted to or screwed in the tip 19a which has a groove 19b in its bottom. The swing reflecting mirror 2 connected with one end of the operative line is pivoted to the mounting piece 20 in a manner so as to freely adjust the angle of reflection. Numeral 21 denotes rotary hobs used for operating the swing reflecting mirror 2, which has a gold plated, mirror finished surface, via the operational wire (not shown). Numeral 22 denotes a telescope fixing barrel which is fixed to the base end of the external tube portion 16b and whose fitting bore 22a receives the forward end 12b of the connection barrel 12 of the rod lens telescope D in a securely fitted manner, and numeral 23 denotes a shaft supporting tube which is perpendicularly arranged on the telescope fixing barrel 22 and through which a drum shaft 24 penetrates in order to freely wind the operational wire thereon and let out therefrom and which is provided with the rotary knobs 21 on both ends thereof.

The tip 11a of the telescope tube portion 11 of the rod lens telescope D is diagonally cut to fit the prism 15 along the cut, thereby securing an angle β of the visibility and a therapeutic region gamma of visibility within the angle β.

The mandrel F is used to open up a closed urethra when starting a treatment and to maintain the operational opening 4b of the outer tube assembly E at a curative region when the bridge B is removed because the swing reflecting mirror 2 has clouded or because one end of the operational wire has come off the swing reflecting mirror 2 after a treatment has started.

The operational wire (not shown) runs through the operational tube 19 of the bridge tube portion 16 of the bridge B. When treating an affected part, the operational wire is wound on the drum shaft 24 or is released from the drum shaft 24 by means of the rotary knobs 21 in order to swing the swing reflecting mirror 2 located in the operational opening 4b and thereby to adjust the angle of reflection.

A preferred embodiment of the present invention will now be described with reference to FIGS. 1A to 4B of the accompanying drawings.

In FIGS. 1A through 4B, reference character A' denotes a prostascope with a bridge, and reference character B' denotes a bridge. Numeral 19a' denotes a threaded end projecting from the tip of an operational tube 19. Numeral 25 denotes a guide member which has a slant guide surface 25a formed at the bottom side thereof for a laser beam emitting end 3a" of a fiber cable 3" and which is fitted to the tip portion of the bridge B' past the threaded end 19a'. The guide surface 25a is disposed at an obtuse angle α relative to the longitudinal axis of the operational tube 19. Numeral 25b denotes a mounting portion which is formed to a cylindrical shape which is integral with and stepped down from the guide member 25, which allows the threaded end 19a' to penetrate therethrough, and which is provided with right and left projecting pins 26 at the base end thereof.

Figure 2:
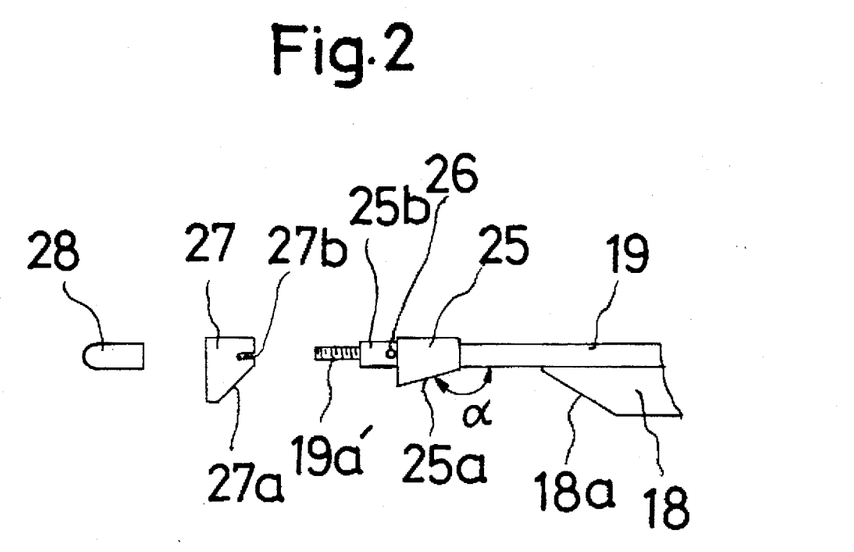
FIG. 2 is a view showing how a reflector according to the embodiment is removable.
Figure 3:
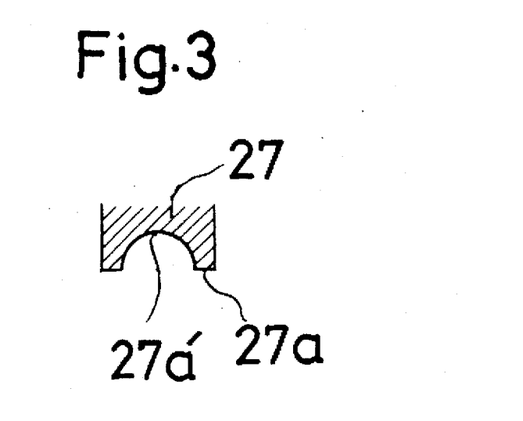
FIG. 3 is an enlarged sectional view of the reflector according to the embodiment.
Figures 4A, 4B:
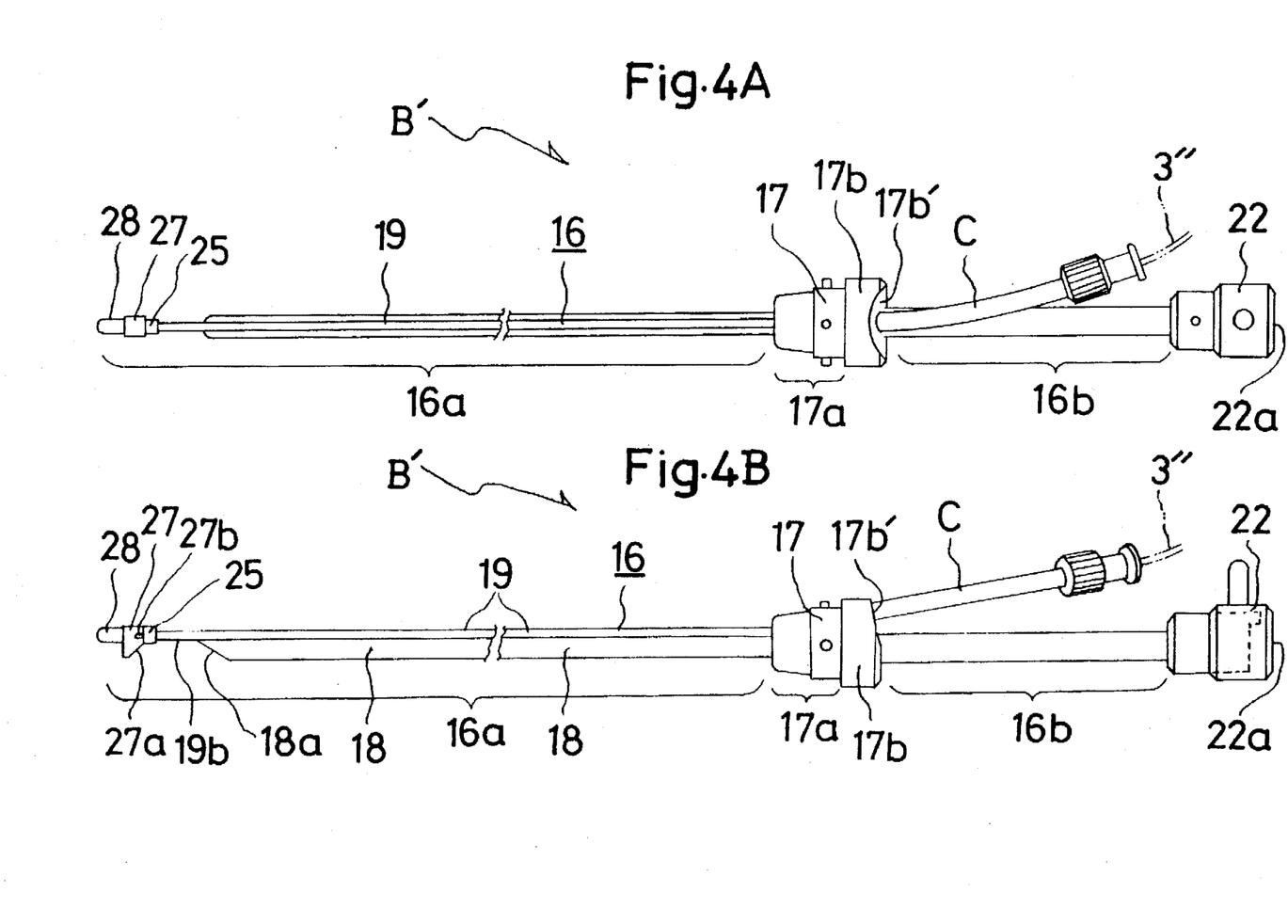
FIG. 4A is a plan view of the bridge according to the embodiment with the intermediate portion thereof omitted.
FIG. 4B is a side view of the bridge according to the embodiment with the intermediate portion thereof omitted.

Numeral 27 denotes a reflector which has a slant reflecting surface 27a having an arbitrary angle of reflection and which is removably fitted to the mounting portion 25b of the guide member 25 past the threaded end 19a'. Numeral 27b denotes securing grooves disposed parallel to the longitudinal axis of the operational tube 19 and which are cut in the reflector 27 at both sides thereof and into which the pins 26 are fitted to prevent the reflector 27 from rotating. Numeral 27a' denotes a reflecting groove surface which is formed in the slant reflecting surface 27a and which has an arcuate cross-section having a radius of curvature of about 1.5°.

Numeral 28 denotes a cap nut which screws to the threaded end 19a' to press and secure the reflector 27 against the guide member 25.

Other portions and members are the same as those of the prior art as shown in FIGS. 2A to 9B and are denoted by common reference numerals. Description of them is therefore omitted to avoid redundancy.

A fiber cable for a general-purpose laser beam (direct projection type quartz fiber cable) can be used as the fiber cable 3". An outer tube assembly of a urethrocystoscope for a Kaiba laser beam (Approval No. 06B-YU-0132) is used as the outer tube assembly E to permit perfusate to flow continuously. The present embodiment is combined with a laser device having the trade name "Yagu Laser Hercules 5040" (Approval No. 04B-YU-0803), for example.

The threaded end 19a', guide member 25, and cap nut 28 are all made of stainless steel. The reflector 27 is usually of brass, and the surface thereof is gold plated and mirror finished. The reflector surface may be plated with silver or copper having a better reflectance according to the type of a laser beam to be used.

Next, the operation of the prostascope having the structure as mentioned above will be described, assuming that the prostascope is used to treat prostatic hypertrophy, for example.

Before starting the treatment, the reflector 27 of an optimum material having an adequate angle of reflection of the slant reflecting surface 27a is attached taking account of the following operative conditions: the part to be treated; angle β of visibility and therapeutic region gamma of visibility of the rod lens telescope D; and the type of a laser beam to be applied.

First, it is confirmed by various diagnoses or inquiries whether or not the patient's urethra is closed. If the urethra is closed, the mandrel F is inserted into the outer tube assembly E and securely set therein as described above. Xylocaine jelly is applied to the closing piece 8 at the tip portion of the mandrel F and the outer surface of the urethral tube portion 4 of the outer tube assembly E. Then, the outer tube assembly E is inserted into the urethra to open it up. Xylocaine jelly is also applied to devices which will be inserted into the urethra in the subsequent procedure.

Figure 1A:
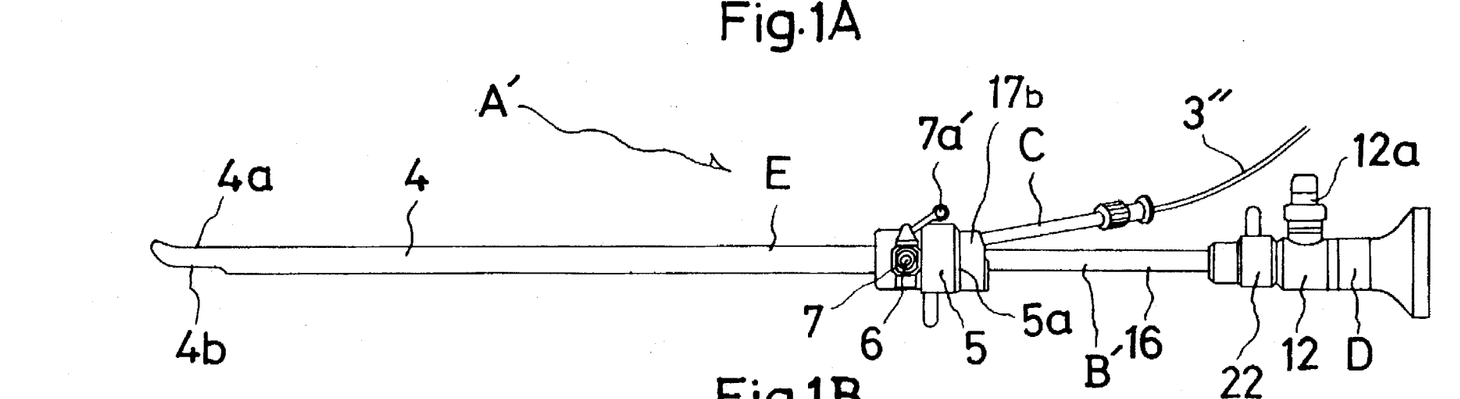
FIG. 1A is a side view of a prostascope with a bridge according to an embodiment of the present invention.
Figure 1B:
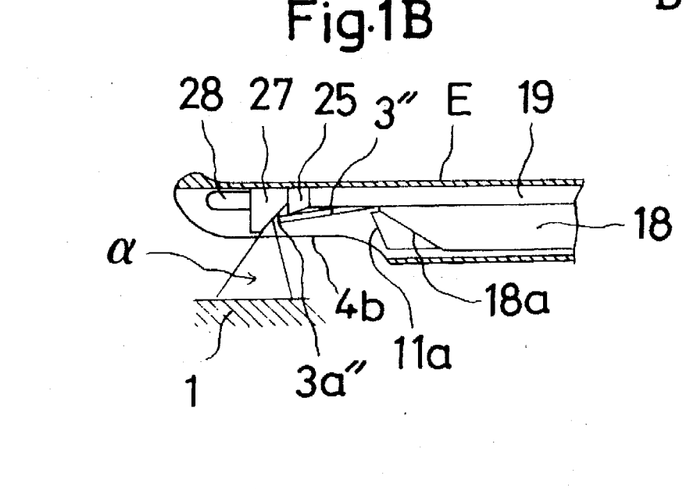
FIG. 1B is an enlarged sectional view of the tip portion of an outer tube assembly according to the embodiment.

Next, the rod lens telescope D is inserted into the bridge B', and the following settings shown in FIG. 1B are established. The laser beam emitting end 3a" of the fiber cable 3" is set and fixed along the slant guide surface 25a of the guide member 25 to face the reflecting groove surface 27a' of the reflector 27. In order to visually recognize an entire affected part irradiated with a laser beam a emitted from the laser beam emitting end 3a" of the fiber cable 3", the diagonally cut tip 11a of the telescope tube portion 11 of the rod lens telescope D is positioned at a location slightly retracted from the slant reflecting surface 27a of the reflector 27 with the laser beam emitting end 3a" of the fiber cable 3" located therebetween. The forward end 12b of the connection barrel 12 is fixedly fitted into the fitting bore 22a of the telescope fixing barrel 22.

Then, the bridge B' with the rod lens telescope D inserted thereinto is inserted into the outer tube assembly E. The cap nut 28, the reflector 27, the laser beam emitting end 3a", the guide member 25, and the diagonally cut tip 11a are set so that they face the operational opening 4b. The forward portion 17a of the junction plug 17 is inserted into the fitting bore 5a of the bridge fixing barrel 5 for fixation thereto. Thus, the prostascope A' with a bridge has been assembled.

Depending on pathology, the prostascope A' may be assembled before the urethral tube portion 4 of the outer tube assembly E is inserted into the urethra.

Under observation through the rod lens telescope D, the assembled prostascope A' is inserted into the urethra from the urinary meatus until the operational opening 4b reaches the affected part 1. A desired therapeutic region gamma is visually determined. While maintaining the thus established state, the user holds the prostascope A' in one hand.

The cocks 7, 7' are opened by operating the cock levers 7a, 7a' with the other empty hand in order to circulate perfusate from the short tubes 6, 6' to the urethra embraced by the prostate. During circulating the perfusate, the treatment of the affected part is started by irradiating it with a laser beam a emitted from the laser beam emitting end 3a" of the fiber cable 3" which is inserted through the fiber guide tube C.

During the surgical treatment, the reflector 27 is advanced or withdrawn by finely sliding the bridge B' forward and backward within the outer tube assembly E. Also, the reflector 27 is moved laterally by finely swinging the bridge B' right and left. Thus, the spot of a laser beam is moved over the affected part 1. If it is necessary to change an angle of reflection to a great extent, the bridge B' is removed from the outer tube assembly E to replace the reflector 27 with the one having the slant reflecting surface 27a of an adequate angle of reflection. Then, the mandrel F is removed from the outer tube assembly E to be replaced with the bridge B'.

Likewise, when the reflecting groove surface 27a' has clouded in the midst of the laser beam surgical treatment, the forward portion 17a of the junction plug 17 is pulled out of the fitting bore 5a of the bridge fixing barrel 5, and then the bridge B' is removed from the bridge fixing barrel 5. The mandrel F is inserted into the outer tube assembly E and the forward portion 9b of the plug 9 is fitted into the fitting bore 5a of the bridge fixing barrel 5, thereby fixing the operational opening 4b of the outer tube assembly E in the urethra at the position of the affected part 1. After polishing the surface of the reflecting groove surface 27a' or replacing the reflector 27, the mandrel F is replaced with the bridge B'.

The user checks the effect of the laser treatment on the affected part 1 through the rod lens telescope D which covers the visual field of the therapeutic region gamma. Then, the user removes the prostascope A' from the urethra to complete the laser-irradiation surgical treatment.

Obviously, numerous modifications and variations of the present invention are possible in light of the above teachings. It is therefore to be understood that within the scope of the appended claims, the present invention may be practiced otherwise than as specifically described herein.

What we claimed is:

1. A prostascope system comprising a prostascope having an outer tube assembly having a distal end with an operational opening and an elongated telescopic tube, a bridge, said telescopic tube being removably disposed on said bridge and having a distal end juxtaposed to said operational opening in said outer tube assembly, said bridge being removably disposed in said outer tube assembly, said bridge comprising an operational tube having a distal end portion disposed at said operational opening in said outer tube assembly, a fiber cable for transmitting a laser beam disposed in said operational tube, said fiber cable having a laser beam emitting end disposed at said operational opening in said outer tube assembly, a reflector, threaded means detachably mounting said reflector on said distal end portion of said operational tube, said reflector having a reflecting surface, a guide member means mounted on said distal end portion of said operational tube, said reflecting surface of said reflector means being spaced from said distal end of said telescopic tube, said guide member means being positioned to be engaged by said fiber cable to guide said laser beam emitting end of said fiber cable to a position facing said reflecting surface and to a position between said reflecting surface and said distal end of said telescopic tube to thereby enable visual recognition via said telescopic tube of the affected part irradiated by the laser beam emitted from said laser beam emitting end of said fiber cable.

2. A bridge according to claim 1 wherein said threaded means comprises threads on said distal end portion of said operational tube and a threaded cap nut engaging the threads on said distal end portion of said operational tube.

3. A bridge according to claim 2 wherein said reflector is slidably received over said threads on said distal end portion of said operational tube, said reflector being disposed between said threaded cap nut and said guide member means.

4. A bridge according to claim 3 wherein said said guide member means has a mounting portion having pins, said reflector having a receiving section receiving said mounting portion of said guide member means, said receiving section having grooves receiving said pins to thereby prevent said reflector from rotating relative to said guide member means.

5. A prostascope system comprising a prostascope having an outer tube assembly having a distal end with an operational opening and an elongated telescopic tube, a bridge, said telescopic tube being removably disposed on said bridge and having a distal end juxtaposed to said operational opening in said outer tube assembly, said bridge being removably disposed in said outer tube assembly, said bridge comprising an operational tube having a longitudinal axis and a distal end portion disposed at said operational opening in said outer tube assembly, a fiber cable for transmitting a laser beam disposed in said operational tube, said fiber cable having a laser beam emitting end disposed at said operational opening in said outer tube assembly, a reflector detectably mounted on said distal end portion of said operational tube, said reflector having a reflecting surface, a guide member means mounted on said distal end portion of said operational tube, said fiber cable having a bent distal end portion disposed at an obtuse angle relative to said longitudinal axis, said distal end portion being bent as said distal end portion engages said guide member means, said reflecting surface of said reflector means being spaced from said distal end of said telescopic tube, said guide member means being positioned to be engaged by said fiber cable to guide said laser beam emitting end of said fiber cable to a position facing said reflecting surface and to a position between said reflecting surface and said distal end of said telescopic tube to thereby enable visual recognition via said telescopic tube of the affected part irradiated by the laser beam emitted from said laser beam emitting end of said fiber cable.

6. A prostascope comprising an outer tube assembly having a distal end with an operational opening, a bridge removably disposed in said outer tube assembly, said bridge including an operational tube having a distal end portion disposed at said operational opening in said outer tube assembly, a fiber cable for transmitting a laser beam disposed in said operational tube, said fiber cable having a laser beam emitting end disposed at said operational opening in said outer tube assembly, a reflector, threaded means detachably mounting said reflector on said distal end portion of said operational tube, said reflector having a reflecting surface, a guide member means mounted on said distal end portion of said operational tube, an elongated telescopic tube means removably disposed on said bridge, said telescopic tube means having a distal end spaced from said reflecting surface of said reflector means, said guide member means being positioned to be engaged by said fiber cable to guide said laser beam emitting end of said fiber cable to a position facing said reflecting surface and to a position between said reflecting surface and said distal end of said telescopic tube means to thereby enable visual recognition via said telescopic tube means of the affected part irradiated by the laser beam emitted from said laser beam emitting end of said fiber cable.

7. A prostascope according to claim 6 wherein said threaded means comprises threads on said distal end portion of said operational tube and a threaded cap nut engaging the thread on said distal end portion of said operational tube.

8. A prostascope according to claim 7 wherein said reflector is slidably received over said threads on said distal end portion of said operational tube, said reflector being disposed between said threaded cap nut and said guide member means.

9. A prostascope according to claim 8 wherein said said guide member means has a mounting portion having pins, said reflector having a receiving section receiving said mounting portion of said guide member means, said receiving section having grooves receiving said pins to thereby prevent said reflector from rotating relative to said guide member means.

10. A prostascope according to claim 9 wherein said mounting portion has a cylindrical configuration, said pins extending radially outwardly from said cylindrical portion.

11. A prostascope according to claim 9 wherein said operational tube has a longitudinal axis, said receiving section of said reflector being slidable over said threads on said distal end portion of said operational tube, said grooves extending generally parallel to said longitudinal axis of said operational tube.

12. A prostascope according to claim 9 wherein said cap nut secures said reflector on said operating tube between said guide member means and said cap nut such that said reflector is readily replaceable on said said operational tube by unscrewing said cap nut from said threads on said operational tube, sliding off the reflector from said operational tube, sliding on a replacement reflector on said operational tube, and threading said cap nut onto said threads on said operational tube.

13. A prostascope according to claim 9 wherein said guide member means includes said mounting portion and a guiding surface portion, said guide member means further comprising a step between said mounting portion and said guiding surface portion.

14. A prostascope according to claim 13 wherein said operational tube has a longitudinal axis, said reflector having a slanting reflecting surface disposed at an obtuse angle relative to said longitudinal axis of said operational tube, and a reflecting groove having an arcuate cross section having a radius of curvative of about 1.5° formed in said slanting reflecting surface.

15. A prostascope comprising an outer tube assembly having a distal end with an operational opening, a bridge removably disposed in said outer tube assembly, said bridge including an operational tube having a longitudinal axis and a distal end portion disposed at said operational opening in said outer tube assembly, a fiber cable for transmitting a laser beam disposed in said operational tube, said fiber cable having a laser beam emitting end disposed at said operational opening in said outer tube assembly, a reflector detectably mounted on said distal end portion of said operational tube, said reflector having a reflecting surface, a guide member means mounted on said distal end portion of said operational tube, an elongated telescopic tube means removably disposed on said bridge, said telescopic tube means having a distal end spaced from said reflecting surface of said reflector means, said guide member means being positioned to be engaged by said fiber cable to guide said laser beam emitting end of said fiber cable to a position facing said reflecting surface and to a position between said reflecting surface and said distal end of said telescopic tube means to thereby enable visual recognition via said telescopic tube means of the affected part irradiated by the laser beam emitted from said laser beam emitting end of said fiber cable, said fiber cable having a bent distal end portion disposed at an obtuse angle relative to said longitudinal axis, said distal end portion being bent as said distal end portion engages said guide member means.

16. A prostascope comprising an outer tube assembly having a distal end with an operational opening, a bridge removably disposed in said outer tube assembly, said bridge including an operational tube having a longitudinal axis and a distal end portion disposed at said operational opening in said outer tube assembly, a fiber cable for transmitting a laser beam disposed in said operational tube, said fiber cable having a laser beam emitting end disposed at said operational opening in said outer tube assembly, a reflector detectably mounted on said distal end portion of said operational tube, said reflector having a reflecting surface, a guide member means mounted on said distal end portion of said operational tube, an elongated telescopic tube means removably disposed on said bridge, said telescopic tube means having a distal end spaced from said reflecting surface of said reflector means, said guide member means being positioned to be engaged by said fiber cable to guide said laser beam emitting end of said fiber cable to a position facing said reflecting surface and to a position between said reflecting surface and said distal end of said telescopic tube means to thereby enable visual recognition via said telescopic tube means of the affected part irradiated by the laser beam emitted from said laser beam emitting end of said fiber cable, said distal end of said telescopic tube means having a distal end surface disposed at an acute angle relative to the longitudinal axis of said telescopic tube means, said guide member means being positioned to be engaged by said fiber cable to guide said laser beam emitting end of said fiber cable in said space between said reflecting surface of said reflector and said distal end surface of said telescopic tube means.

* * * * *